(12) United States Patent
Iuliano (10) Patent No.: US 7,209,773 B2
(45) Date of Patent: Apr. 24, 2007

(54) METHOD AND APPARATUS FOR PERFORMING IN-VIVO BLOOD ANALYSIS USING RAMAN SPECTRUM

(75) Inventor: Michael J. Iuliano, Point Pleasant Beach, NJ (US)

(73) Assignee: In Technology Holdings LLC, Toms River, NJ (US)

( * ) Notice: Subject to any disclaimer, the term of this patent is extended or adjusted under 35 U.S.C. 154(b) by 218 days.

(21) Appl. No.: 10/872,033

(22) Filed: Jun. 18, 2004

(65) Prior Publication Data
US 2005/0288564 A1 Dec. 29, 2005

(51) Int. Cl.
*A61B 5/00* (2006.01)
(52) U.S. Cl. .................... 600/318; 600/310; 600/322
(58) Field of Classification Search ............ 600/310, 600/318, 322
See application file for complete search history.

(56) References Cited

U.S. PATENT DOCUMENTS

2001/0034478 A1* 10/2001 Lambert et al. ............ 600/318

* cited by examiner

*Primary Examiner*—Eric F. Winakur
*Assistant Examiner*—Jack Lin
(74) *Attorney, Agent, or Firm*—Gottlieb, Rackman & Reisman, P.C.

(57) ABSTRACT

An in-vivo blood composition analyzing apparatus and method generates a laser beam at the blood vessels of the patient's eye. The Raman scattered photons from the blood vessels are collected and used to generate a Raman spectrum indicative of the blood composition. In one embodiment, a laser beam is generated with two streams of photons, the photons of one beam being entangled with the photons of the other beam. One stream is then directed at the eye and only the other beam is analyzed to obtain said Raman spectrum. Alternatively, the scattered photons from the second beam are also analyzed and the results are correlated for greater efficiency and accuracy.

16 Claims, 8 Drawing Sheets

Laser Tracking Pattern

Figure 2

14 A
Digital Pixels
of Conjunctival
Blood Vessels

METHOD AND APPARATUS FOR PERFORMING IN-VIVO BLOOD ANALYSIS USING RAMAN SPECTRUM

RELATED APPLICATIONS

METHOD AND APPARATUS FOR DETECTING CHEMICAL & BIOLOGICAL WEAPON COMPONENTS USING RAMAN SPECTRUM, Ser. No. 10/872,032 filed on even date herewith, now U.S. Pat. No. 7,116,415.

BACKGROUND OF THE INVENTION

1. Field of Invention

The present invention describes a system and method for performing in vivo blood analysis. This is accomplished by directing a probe beam, consisting of monochromatic, coherent, polarized, quantum state entangled, exclusive or nearly exclusive co-incident photons, at the conjunctiva and its blood vessels of a patient and analyzing the resulting conventional Raman backscatter spectrum and the changes in the quantum state characteristics of the entangled photons.

2. Background of the Invention

Various blood chemistry and hematology tests are available to obtain a great amount of information about a patient's physical condition. These results, after review and interpretation, play an important part in an overall diagnosis. However, all these tests require actual samples taken from a patient. Of course, the process of drawing blood, can be uncomfortable, and even painful, especially if constant repetitive sampling is necessary as in the case of diabetics.

For this reason non-invasive in vivo blood studies by optical devices and methods have been investigated with great interest. The determination of an analyte, or a disease state, in a human subject without performing an invasive procedure, such as removing a sample ,of blood or a biopsy specimen, has several advantages. These advantages include ease in performing the test, reduced pain and discomfort to the patient, decreased exposure to potential biohazards, and no production of medical waste. These advantages encourage increased frequency of testing when necessary, accurate monitoring and control, and improved patient care. Representative examples of non-invasive monitoring techniques include pulse oximetry for oxygen saturation (U.S. Pat. Nos. 3,638,640; 4,223,680; 5,007,423; 5,277,181; 5,297,548). Another example is the use of laser Doppler flowmetry for diagnosis of circulation disorders (Toke et al, "Skin microvascular blood flow control in long duration diabetics with and without complication", Diabetes Research, Vol. 5 (1987), pages 189–192). Other examples of techniques include determination of tissue oxygenation (WO 92/20273), determination of hemoglobin (U.S. Pat. No. 5,720,284) and of hematocrit (U.S. Pat. Nos. 5,553,615; 5,372,136; 5,499,627; WO 93/13706). These involve the use of transmission, or absorption spectroscopy.

Another type of phenomena can also be used for patient testing. This involves the way in which light scatters off any surface. That is to say, when light of any wavelength impinges on a surface (or molecule), most of the scattered photons are elastically (or Rayleigh) scattered. That means that they leave with the same frequency (or wavelength) as the incident radiation. In contrast to this there is a small fraction of the scattered light (less than one in a thousand incident photons) that is inelastically (or Raman) scattered at frequencies that differ from the incident frequency by a value determined by the molecular vibrations of the sample.

Raman scattering creates a discrete atomic or molecular spectrum at frequencies corresponding to the incident frequency plus or minus the atomic or molecular vibrational frequency. A Raman spectrum is thus a plot of the intensity of scattered light as a function of frequency (or wavelength). By convention, Raman spectra are shown on an orthogonal graph with the wave numbers (reciprocal centimeters) along the horizontal axis and the abscissa representing intensity or energy.

Raman spectra have long been used to determine the structure of inorganic and biological molecules, including the composition of complex multicomponent samples. Raman spectroscopy is considered to have many advantages as an analytical technique. Most strikingly, it provides vibrational spectra that act as an atomic o,r molecular fingerprint containing, unique, highly reproducible, detailed features, thereby providing the possibility of highly selective determinations.

In comparing Raman scattering verses other forms of analysis, the Raman approach is advantageous for several reasons:

1. Solid, liquid and gas states can be analyzed.
2. Aqueous solutions present no special problems.
3. No special pre-scanning preparation of the sample is necessary.
4. The low frequency region is easily obtained.
5. The device can be made inexpensive lightweight and portable.
6. Scanning can be completely non invasive or even clandestine.
7. Scanning distance can be varied from centimeters to kilometers.

Several previous inventors have recognized the potential for using Raman scattering as a non-invasive (NI) sensor for scanning individuals. U.S. Pat. No. 6,574,501 discusses assessing blood brain barrier dynamics or measuring selected substances or toxins in a subject by analyzing Raman spectrum signals of selected regions in aqueous fluid of the eye. U.S. Pat. No. 5,553,616 discloses the use of Raman scattering with excitation in the near infrared (780 nm) and an artificial neural network for measuring blood glucose. WO 92/10131 discusses the application of stimulated Raman spectroscopy for detecting the presence of glucose. U.S. Pat. No. 6,070,093, describes a noninvasive glucose sensor that combines Raman measurements with complementary non-invasive techniques in order to enhance the sensitivity and selectivity of the measurement.

Other previous inventors have recognized the potential for using Raman scattering for non-invasively scanning of objects. U.S. Pat. No. 6,608,677 discloses the use of a Mini-lidar sensor for the remote stand-off sensing of chemical/biological substances and method for sensing same. U.S. Pat. No. 6,593,582 discloses a Portable digital lidar system, which in part could use raman backscattering. U.S. Pat. No. 4,802,761 discusses optical-fiber Raman spectroscopy used for remote in-situ environmental analysis.

Still other previous inventors have recognized the potential for using SPDC (Spontaneous Parametric Down Converstion) photons for enhancing the scanning of objects. U.S. Pat. No. 5,796,477 discloses an entangled-photon microscope, for waveform fluorescence microscopy.

A major challenge for all of the Raman techniques to date has been to collect spectral information with sufficiently high signal-to-noise ratios to discriminate weak analyte signals from the underlying background noise.

Existing non-invasive in vivo Raman measurements are hindered by a number of factors, including notoriously low quantum efficiency. In other words, very few inelastic scattering events occur in comparison to the number of elastic scattering events. Conventionally, in non-resonance Raman spectroscopy in order to double the efficiency of Raman scattering it is necessary to square the photon density. Unfor-tunately this can damage the sample. Therefore it is necessary to perform scans at either long integration times or high power densities to achieve acceptable signal-to-noise (S/N) ratios.

Other forms of Raman scattering like, resonance and surface enhancement can significantly improve the sensitivity and selectivity of Raman measurements. However, these enhancements are not generally applicable to all analytes or to all samples, especially in vivo. Furthermore relating band intensities to analyte concentrations under such circumstances requires careful calibration procedures.

SUMMARY OF THE INVENTION

Briefly, the present invention pertains to a system and method in which a laser beam preferably near the infrared region, is generated and used to analyze the blood of a patient in vivo. In one embodiment, the laser beam is directed by a tracking system toward the blood vessels of an eye and the resulting Raman back scatter is intercepted, collected and analyzed. The beam, in this case, could include a photon stream that has been downconverted from a high energy level into two coincident lower energy level streams using SPDC or other known entanglement methods. In one embodiment of the invention, the blood vessels of the eye are located and the beam is directed by a tracking system to follow the blood vessels for a time period sufficient to collect the necessary Raman back scatter. In another embodiment, the tracking system is used to direct the beam across the surface of the eye and filtering is used to detect only Raman back scatter corresponding to any blood vessels. In either case, tracking system insures the beam never enters the eye and is kept away from the pupil. Moreover, the intensity of the laser beam is kept at a low level known to be safe.

In still another embodiment of the invention, the laser source uses SPDC or other known phenomena to generate pairs of entangled photons. The paired photons are separated into corresponding photon streams, one stream including one photon of each entangled pair, and the other stream including the other photon of each entangled pair. One stream is then directed by the tracking system at the patient's eye, while the other stream is directed at a remote detector set up to measure changes in entangled quantum state characteristics. Polarization detection is a common technique used in both Raman spectroscopy and also quantum state transfer analysis.

Raman backscatter is by nature partially polarized, even for molecules in a gas or liquid state, where the individual molecules are randomly oriented. Raman backscatter from totally symmetric vibrations will be strongly polarized parallel to the plane of polarization of the incident light. The scattered intensity from non-totally symmetric vibrations is ¾ as strong in the plane perpendicular to the plane of polarization of the incident light as in the plane parallel to it.

By carefully creating the down converted beams to have their polarization entangled, the quantum state changes in polarization which occurs in the probe beam, at the level of the sample, as a function of Raman backscatter, will be transferred to the remote detector beam. When the geometry of the system is set to read fractional depolarization per specific frequency, the unique finger print vibrational modes of an analyte can be determined. This makes it possible to obtain certain blood analyte concentrations without actually collecting and analyzing the Raman back scattered photons. In another embodiment, both conventional backscatter and the remote detector streams are analyzed and the results are correlated for increased redundancy and accuracy.

DETAILED DESCRIPTION OF THE INVENTION

The present invention describes a system and method for performing in vivo blood analysis. This is accomplished by directing a probe beam (such as a monochromatic, coherent, polarized, quantum state entangled, exclusive or nearly exclusive co-incident photon beam) at the conjunctiva and its blood vessels of a patient and analyzing the resulting conventional Raman backscatter spectrum and the changes in the quantum state characteristics of the entangled photons.

It is well known, in Raman spectroscopy, that in order to improve the quantum efficiency, it is necessary to increase the photon density. But the relatively high power densities used in this technique can cause tissue damage or destruction, which is unacceptable, especially in a highly critical organ, such as a person's eyes. The high power density may also induce black body interference, due to heating by the laser, which may further obscure the Raman spectrum.

An intuitive solution would be to attenuate the laser power to the point where the power density is below the tissue damage or destruction level. The major drawback with this approach is that the "normal" or intrinsic amount of Raman scattering has very low efficiency and therefore produces a weak signal in the first place. Attenuating the signal further can cause the loss of the Raman spectrum in the background noise. This is due to the fact that Raman backscatter intensity is directly related to the total number of photons impinging on the sample. Therefore, any reduction in laser power to the sample must be counterbalanced by increasing the acquisition time. This leads to acquisition times that can reach hours per sample versus seconds or minutes. Another problem is that the natural phosphorescence of the blood induced by a probe beam interferes and masks Raman backscattering and makes it more difficult to distinguish the resultant Raman spectrum. Thus there is a need for an apparatus and method of making quick, accurate, and reliable in vivo blood analysis using Raman spectrums.

The present invention provides several solutions to this problem that can be utilized concurrently or independently of each other. More particularly, according to the present invention, the probe beam is not directed at a particular ocular blood vessel section for an extended time period but, instead, it is substantially continuously moving, thereby reducing the time during which any particular blood vessel section is exposed thereto. The photons scattered by the blood vessels are collected and analyzed to determine various characteristics of blood flowing therein. One major advantage of the invention is that, the ocular blood vessels disposed in the subconjunctival space are very close to the surface of the eye. In fact, typically these vessels are about 0.5 mm below the tear film on the eye and the overlaying conjuntival tissue. Blood vessels in the other part of the body can be positioned 3–5 mm below the surface of the skin. Therefore, subconjunctival blood vessels are much more accessible.

Another major advantage is that both the tear film and the conjunctival tissue covering the ocular blood vessels are substantially transparent to NIR. In contrast, subcutaneous blood vessels are covered by skin and other tissues that are more opaque to near infrared (NIR) and cause signal attenuation and also the production of significant confounding Raman spectrum.

A third advantage is that since blood is not stationary but flows through the blood vessels, and since the blood has substantially uniform consistency, data collected from many readings along the blood vessels can be gathered and used collectively for the blood analysis. In other words, measurements obtained from different blood vessel sections at different times can be combined and used in the determination of the desired blood parameter. The motion of the blood also helps prevents excessive power density exposure to any one particular area of tissue.

Figure 1:
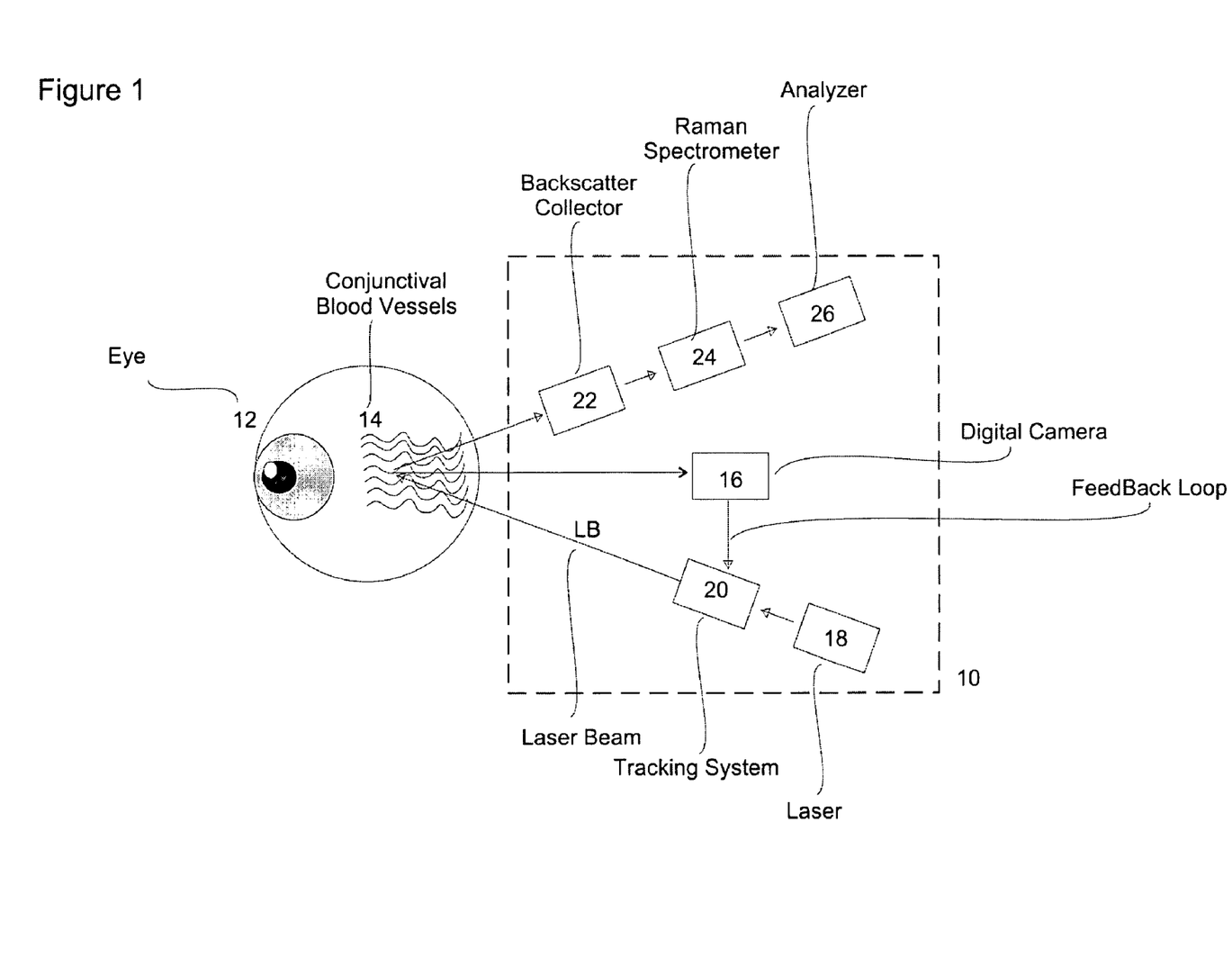
FIG. 1 shows a block diagram of the apparatus used for performing blood analysis in accordance with this invention.

FIG. 1 shows one embodiment of the invention. In this embodiment, apparatus 10 is used to make measurements in the eye 12 of a patient, and more particularly, to measure certain characteristics associated with the conjunctival blood vessels 14. In this embodiment, the apparatus 10 includes a digital camera 16, a laser 18, a tracking system 20, a photon collector such as a backscatter collector 22, a Raman spectrum generator and/or a Quantum state characteristic generator 24 and an analyzer 26. Of course some of these elements could be combined into a single microprocessor-based apparatus, however, discrete elements are being shown for the sake of clarity.

Figure 2:
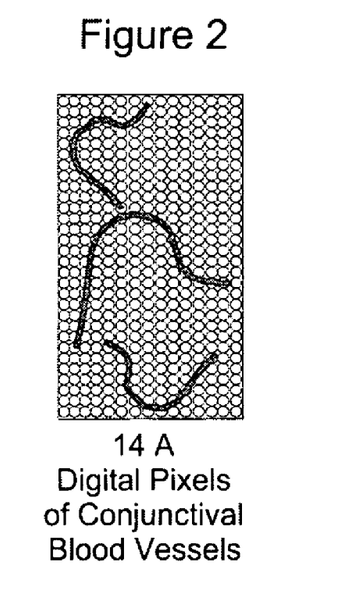
FIG. 2 shows a digital image of an eye with blood vessels.
Figure 3:
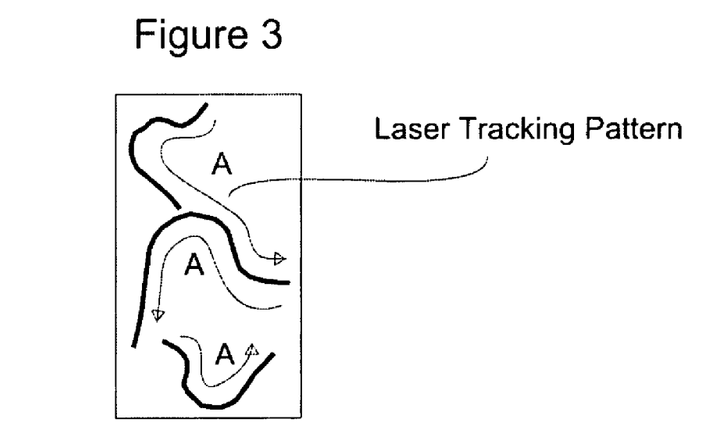
FIG. 3 shows a pattern followed by a laser beam on the eye.

The digital camera 16 is used to locate and identify the positions of the blood vessels 14. The camera 16 takes a digital picture of a portion of the eye with blood vessels 14A as shown in FIG. 2. This picture is provided to the tracking system 20. The tracking system 20 receives a laser beam LB from laser 18 and directs it toward the eye 12. More particularly, the tracking system 20 uses the information from the digital picture of FIG. 2 to direct the probe beam in either a continuous pattern along the blood vessels as shown in FIG. 3 as indicated by arrows A, or some other pattern designed to expose the blood vessels to the probe beam.

Figure 4:
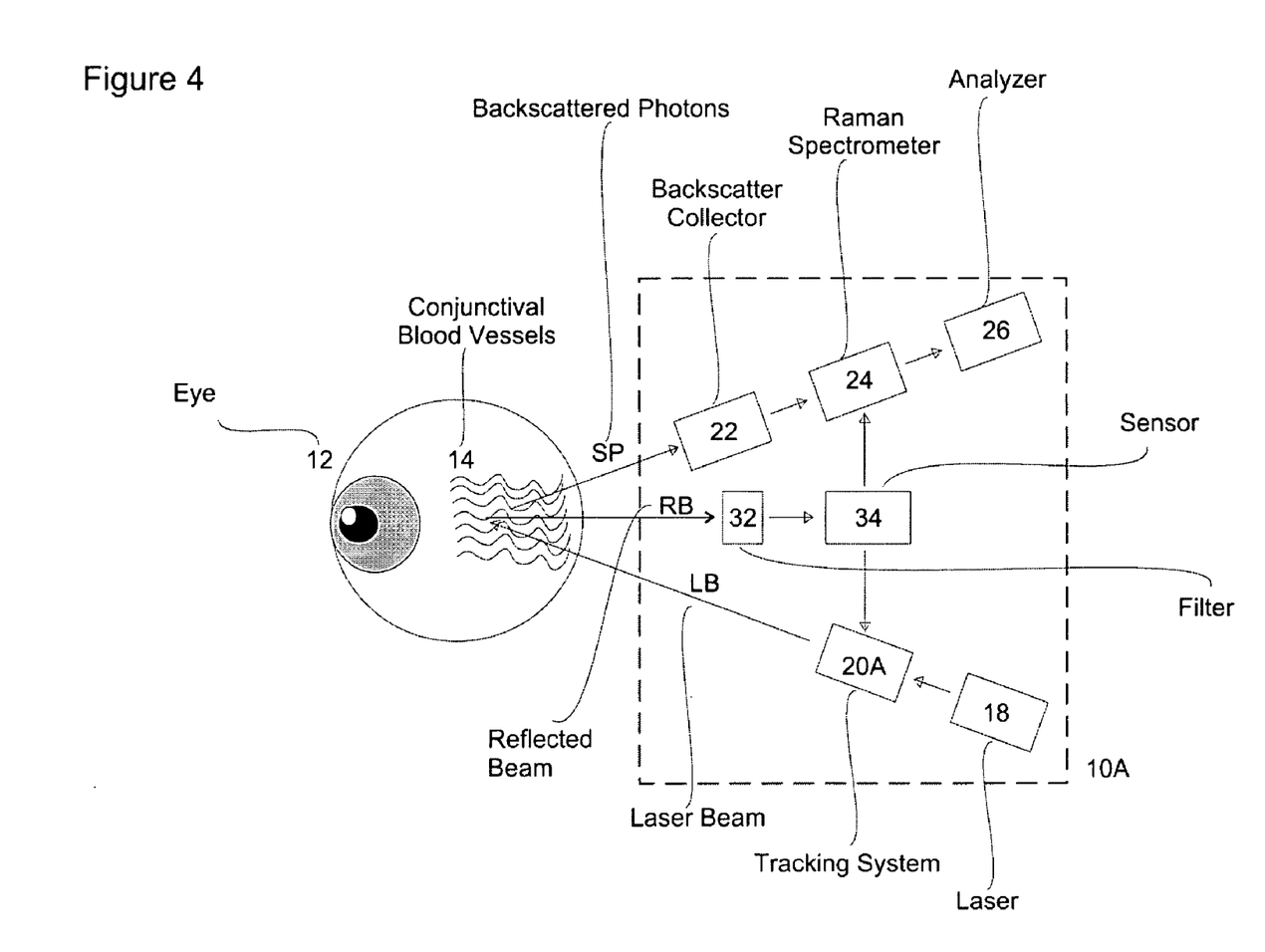
FIG. 4 shows a block diagram of an alternate embodiment for the apparatus of FIG. 1.

FIG. 4 shows an alternate embodiment. In this embodiment, an apparatus 10A for analyzing blood includes similar elements to the apparatus 10 in FIG. 1, with the exception that the digital camera 16 is replaced with a filter 32 and a sensor 34. In this embodiment, tracking system 20A at least initially directs the laser beam LB at the eye 12 in a pattern designed to cover a large area thereof. The reflected beam RB from the eye passes through a filter 32 and the filtered beam is intercepted by a sensor 34. The filter 32 and the sensor 34 are arranged to detect when the beam is reflected from a blood vessel 14. In one embodiment, the photon detector 22 monitors the scattered photon beam SP. When the photon detector 22 receives an indication that the laser beam LB is impinging on a blood vessel, the photon detector processes the photons. Otherwise, the photons of beam SP are ignored. In another embodiment, the tracking system scans the visible portion of the eye, a signal indicating when the beam LB impinges on the blood vessel. The tracking system then uses this input to generate a map similar to the digital image of FIG. 2 indicating the position of the blood vessels. Once the scanning of the eye is completed, the scanning system 20A starts directing the probe beam LB only at the blood vessels along a path as shown in FIG. 3. In other words, the tracking system falls back to the operation described in conjunction with FIG. 1.

Tracking systems for tracking the eye of a patient and to direct a laser beam at the eye are well known in the art. Eye tracking devices vary greatly in speed depending upon their type. For the present invention, depending on the particular embodiment, the predictability of the blood analysis outcome could be affected by the accuracy of the eye tracking system being used. The eye tracking system must be able to sample the eye's position at a rate of at least 1,000 times per second to keep up with the saccadic movements which can happen up to 100 times per second.

Tracking systems use either a closed loop control scheme, or an open loop control scheme. In a closed loop system the tracking system uses an active feedback control mechanism for verification of the laser aiming positions before releasing the laser pulses. One well-known eye tracking system that is commercially available for Lasik (for refractive surgery) is called the LadarVision system available through Alcon. This system measures eye movements at a rate of 4,000 times per second and is locked on the eye at all times. Eye movement information is continuously relayed to the system, allowing the system to compensate for the movements in an appropriate time scale to position treatment pulses (or for the purposes of this invention scan pulses) at the desired location.

The other prominent eye movement tracking system is based on an open loop video tracking. In these systems, Tracking is implemented by using reflections of an infrared light source from the front and rear surfaces of the cornea and lens (Purkinje images). Alternative features that may also be used include the boundaries between white sclera and iris (limbus tracking) and between the iris and pupil (pupil tracking).

The following are examples of U. S. Patents which disclose known eye tracking systems:
1. 6,322,216: Two camera off-axis eye tracker for laser eye surgery
2. 6,702,809: System for detecting, measuring and compensating for lateral movements of a target
3. 6,598,971: Method and system for accommodating pupil non-concentricity in eyetracker systems
4. 6,659,611: System and method for eye gaze tracking using corneal image mapping
5. 5,410,376: Eye tracking method and apparatus
6. 4,287,410: Double Purkinje eye tracker Referring back to FIG. 1, once the positions of the blood vessels 14 are identified, an laser beam LB is generated by the laser beam generator 18. This laser beam LB is then directed at the blood vessel by the tracking system 20. Any one of the open or closed loop tracking systems discussed above can be used as the tracking system 20 in FIG. 1. Of course, the systems are modified to maintain fixation on the blood vessels as identified by the digital image of FIG. 2. This fixation has to be maintained long enough to either scan the blood vessels along the lengths of the blood vessels, for example using the pattern shown in FIG. 3, or using some other (possibly random) pattern to scan various portions of the blood vessels for short time periods to insure that the blood vessels and the eye tissues remain intact and are not damaged.

In a preferred embodiment of the invention, a relatively rudimentary eye position monitoring system is used that is tracking just the gross position of the eye, so as to allow a scan of the entire conjunctival area. In this embodiment, tissue signals that are of no interest can be discarded. As before, an important feature of the invention is that the eye position monitor system operates to insure that at no time is the beam directed into the eye itself.

The probe beam controlled by the eye tracking system, typically may have a wavelengh in the range of about 700–1400 nm and a power level not to exceed the Maximum permissible exposure of the retina. (See U.S. Pat. No. 6,574,501 for an extensive review of permissible retinal power density per frequency). The probe beam incident on the blood vessels 14 results in Raman backscatter in the known manner. The Raman back scatter is gathered by photon collector 22. The detected signals from collector 22 are then sent to Raman spectrum generator and polarization analyzer 24 that generates a Raman spectrum and quantum change characteristics profile of the contents blood vessels 14. The Raman spectrum and quantum change characteristics (including, optionally, polarization information) profile is fed to an analyzer 26 which analyzes these characteristics characteristics profile using algorithms known from prior art. This generates an output indicative of the desired measurements or parameters of interest, related, for example to sugar levels, cholesterol levels, etc.

As explained above, Raman backscatter is normally difficult to detect because of the high signal-to-noise ratio of the environment from which it gets collected. The present invention provides several methods of solving this problem. The first method pertains to the frequency of the excitation used to create Raman backscatter. More specifically, the probe beam generated by the probe beam generator 18 has a wavelength selected preferably in the NIR region of about 700–1400 nanometers. This wavelength range insures that interference with fluorescence is reduced. Further reducing confounding fluorescence can be achieved by continuously moving the probe beam across the sample while pulsing the beam. Since Raman backscatter and fluorescence (the decay of long-lived electronic excitations) have different time delays, the extended shouldering of the fluorescence can be effectively ignored from each new sample zone.

The second method is to increase the number of photons in the probe laser beam that reach the sample simultaneously while reducing the photons that do not add significantly to the production of the Raman back scatter. Unlike conventional Raman, which uses massive photon volume to achieve a "random co-incidence" of photons in its signal production, the embodiment of this device is to produce a beam of photons that already share the same temporal and quantum state. That is, a portion of the highly energetic photons of the initial pump beam laser undergoes Spontaneous Parametric Down Conversion (SPDC) into two photons of lower energy, in such a way that all or nearly all the photons of the new probe beam are overlapped or co-incident in space and time. This in effect changes the doubling of Raman emission efficiency from the square of the density of the photon beam to a linear function. This is because almost all the photons which produce the Raman effect at low efficiency have been replaced with co-incident photons which have a much better probability of producing Raman back scatter. This also has the beneficial effect of decreasing the overall energy introduced to the tissue.

Figure 5:
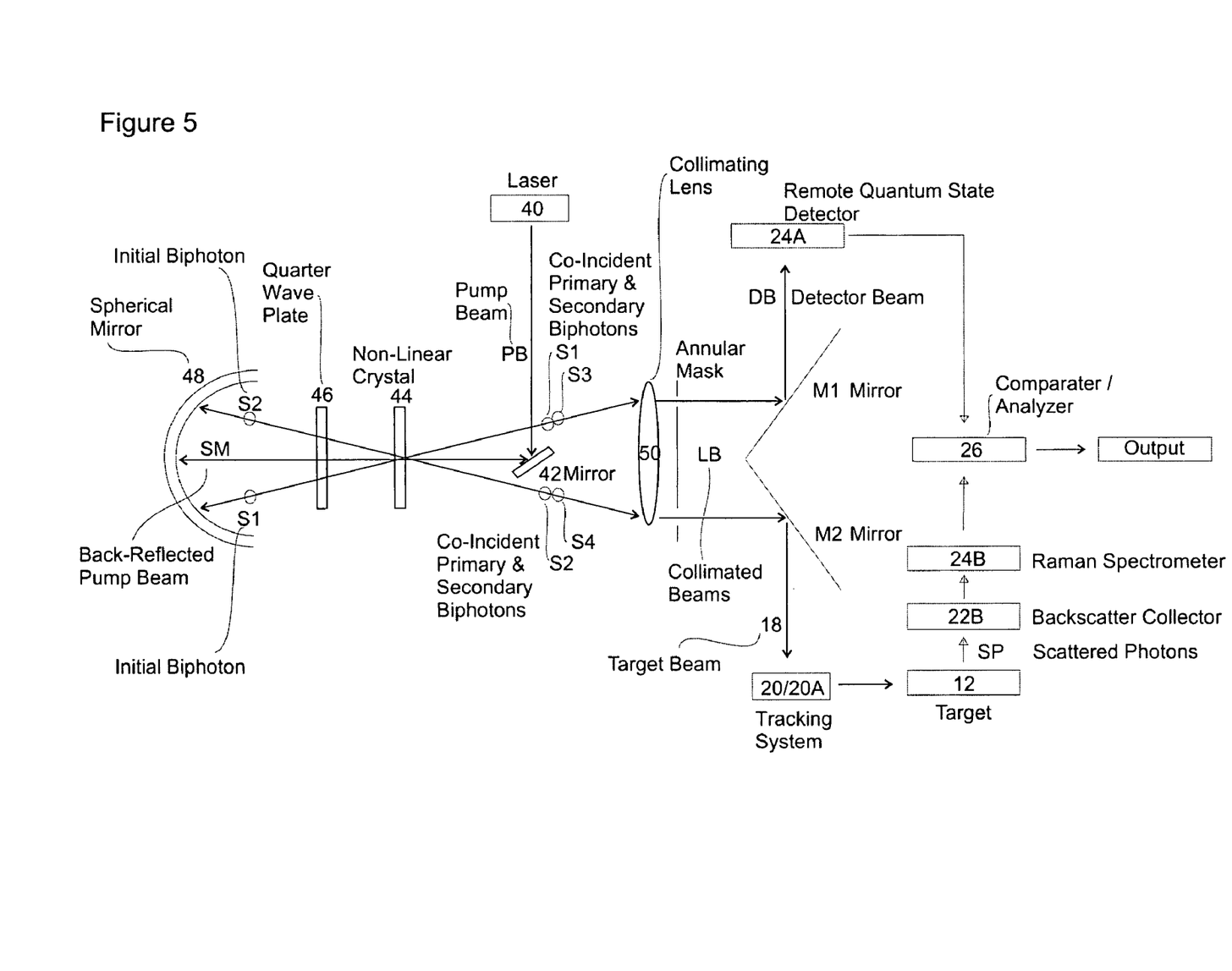
FIG. 5 shows a block diagram of a laser pump beam undergoing SPDC to generate the probe beam used in the apparatus of FIGS. 1 or 4.
Figure 6:
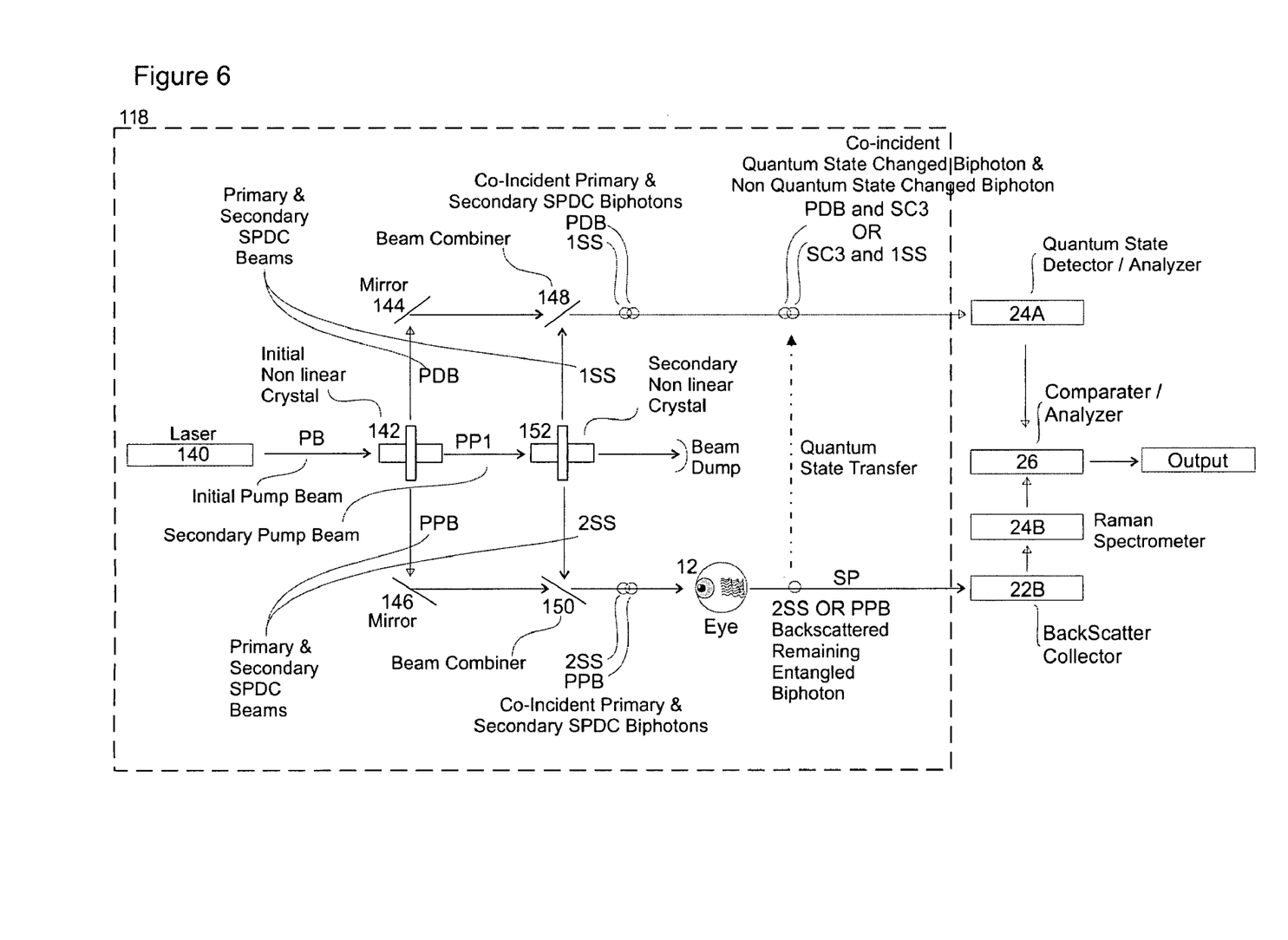
FIG. 6 shows a block diagram of an alternate method in which the laser pump beam undergoes SPDC to generate the probe beam used in the apparatus of FIGS. 1 or 4.

The third method is to utilize the fact that when highly energetic photons undergo SPDC they split into a pair of lower energy photons that share entangled quantum states, commonly polarization and/or frequency. By carefully setting the geometry of the SPDC photon production, two separate beams of co-incident quantum state entangled photons can be created, each containing one half of the original quantum state entangled photon pair sitting in superposition with other similar photons. One stream, the probe beam, is applied to a section of blood vessels, and the resulting Raman spectrum is determined from the characteristics of the conventionally backscattered photons. The second beam is sent on to a remote detector. Due to the fact that the second photon stream is quantum state entangled with the primary probe beam, it will undergoes the same quantum state change as its entangled pair in the probe beam. Since the remote detector beam never interacts with the sample is not affected by noise, thereby making the change in quantum characteristics much easier to extract. Two apparatus demonstrating these principles are shown in FIGS. 5 and 6, FIG. 5 shows a somewhat preferred of many configurations creating a probe beam formed of quantum state entangled co-incident photons through SPDC (See U.S. Pat. No. 6,424,665 and article G Giorgi et al; A High Brightness Parametric Source of Entangled Photon States). It includes a pump laser 40 generating a pump beam PB. The pump beam is directed to a mirror 42 that directs it through a type I non-linear crystal 44 made of $BaB_2O_4$ (BBO) and having a 32.6 degree orientation, a quarter-wave plate 46, a spherical mirror 48 having a radius equal to its distance to the crystal 44, and a collimating lens 50.

There are several well known lasers that can be used for the pump 40. Some of these are listed below.

Quantum Stack Laser
Gas Laser
Dye Tunable Laser
Semi Conductor Laser
Diode Laser
Quantum Dot laser The Quantum Stack laser or multi-frequency Quantum Dot laser is particularly suitable as the pump beam generator because it can be set to produce beams at several discrete frequencies simultaneously. This becomes important as an additional method to improve the signal to noise ratio. As mentioned above, Raman spectra is a reflection of the vibrational state of a molecule plus or minus the frequency of the incident light. In a complex multicomponent sample, background fluorescence and spectral signals of components of non-interest can overlap the spectral signal of the component of interest. In order to further reduce these confounding signals it is advantageous to use probe beams of several frequencies that are carefully chosen to produce spectra of the analyte where different confounding signals may present but not initial confounding signals. It should be noted that multiple frequencies are especially helpful with extracting Raman from over lapping fluorescence. This is because that although the fluorescence spectrum is shifted from the laser frequency, the fluorescence shift depends on the laser frequency whereas the Raman shift does not. After differential subtraction is applied to the two frequency spectra, Raman spectra become separated from fluorescence signals. Then, multivariate analysis can be applied to the resultant frequency spectra. This in turn will lead to a higher confidence level.

The probe beam generator 18 is represented in FIG. 5 as a laser 40 and operates as follows. Generally speaking, the probe beam generator 18 makes use of a single-arm interferometer to create probe beam LB comprising monochromatic coherent polarized exclusively or nearly exclusive co-incident photon pairs. The primary beam is reflected by mirror 42 through crystal 44 and plate 46 unto mirror 48. Mirror 48 returns this beam as a secondary beam SM through the plate 46, crystal 44 and mirror 42 to the laser 40. Crystal 44 causes a portion of both the primary and the secondary beams to undergo spontaneous parametric down-conversion as they pass therethrough. The geometry of SPDC generates a pair of coincident conically shaped beams linearly polarized. All (SPDC) photon pairs are emitted at a predetermined wavelength, in this case of 727.6 nm. Two beams of photons S1 and S2 resulting from the pumped beam PM hit the mirror 48. These beams S1, S2 are returned to lens 50 and have arc shape. In addition, the secondary beam SM causes the generation of two more beams of photons S3 and S4. These latter beams are coincident in time and space with the beams S1, S2 respectively and are also coincident on the lens 50 as shown. In one embodiment of the invention, the lens 50 coverts the photon beams S1, S2, S3, S4 into a single colimated ring shaped laser beam LB. This beam LB is more effective then standard beams because it constitutes two sets of coincident photons S1, S3 and S2, S4 generated as discussed above.

However, preferably, the detector also takes advantage of the fact that the beams resulting from lens 50 contain entangled photon pairs. The importance of entangled pairs of photons is that the state of one photon of a pair can be determined from the state of the other, even if great distances separate the photon pairs. Thus, a detector system can be constructed in which the entangled photon pairs are separated, and then one photon (from a probe beam) is sent toward the sample and the second photon (from a detector beam) is sent towards a remote detector. The probe beam photons that strike the sample undergo Raman back scattering and the change in their quantum state is transferred to the corresponding entangled photons in the remote detector beam. In conventional Raman backscatter photons scatter in all directions but only the photons that bounce directly back to the detector can be collected and analyzed. In contrast, quantum entanglement detection allows one to determine the quantum status of all the photons of the probe beam independently of the direction in which they scatter, or even need of collecting the any of the conventionally scattered photons at all. Thus, while in a conventional Raman back scatter device, only about 25% of the photons are collected and analyzed, in a Raman back scatter detector using entangled photons, all 100% of the photons are available for quantum state analysis. Moreover, if the backscatter photons are collected in the conventional manner described above, and their quantum state is also analyzed, the two results may be combined. This means that the upward of 125% of the actual quantum state changes are available to delineate molecular structure in addition to the conventional Raman spectrum.

Referring back to FIG. 5, instead of collimating the beams, S1, S2, S3 and S4, two mirrors M1 and M2 are used to direct these beams in different directions. More particularly, the photon beams S1, S3 form the detector beams that are directed toward a detector such as the Raman spectrum generator and polarization analyzer 24A similar to generator 24 in FIG. 1. The photon beams S2, S4 form the probe beam that is directed to the patient's eye 12 and their status can be determined from the detector beam since the photons S2, S4 are entangled respectively with the photons S1, S3. Alternatively, the photons back scattered from eye 12 can be collected and directed at backscatter collector 22B and polarization analyzer 24B. The results from two generators 24A, 24B can be collated or combined to determine the Raman spectrum with even more certainty. In yet another embodiment of the invention, the mirror 48 is replaced by lens 50. In this embodiment, only primary entangled photon beams S1, S2 are generated. Since the photons of these beams are still entangled, they can still be used to form respective probe and detector beams. However, since the secondary beam SM is omitted the Raman effect will be greatly reduced because no superposition photons exist in the probe beam.

Referring now to FIG. 6, an alternate embodiment of a laser beam generator 118 incorporating these principles includes a laser 140 that generates a primary pump beam PB for an optical element such as an initial non linear crystal 142. Element 142 may be, for example, a type, I (idenically polarized signal and idler photons) SPDC crystal in a single-mode nonlinear waveguide pumped by a beam perpendicular to the wave guide. Element 142 generates a primary detector beam PDB, a primary probe beam PPB, and an attenuated secondary pump beam PP1. Mirrors 144 and 146 direct beams PDB and PPB towards mirrors 148, 150 respectively. Pump beam PB2 is directed at a second optical element 152. Element 152 generates from pump beam PB2 two secondary streams 1 SS and 2SS consisting of a respective photon of the entangled photon pairs. Mirrors 148, 150 are structured so that they allow the transmission of the respective primary beams and reflect the secondary streams 1SS and 2SS. Each of these beams combine with the respective coincident beams from mirrors 144, 146. Thus the beams from mirrors 148, 150 have similar structures to the two beams from lens 50 in FIG. 5. The beam from mirror 148 could be the detector beam directed Entangled Quantum Characteristic Detector 24A, while the beam from the mirror 150 could be the probe beam directed at eye 12. The result from generator 24A can be used in its own. Alternatively, the photons scattered from the eye 12 are collected and used by generator 24B to obtain another Raman spectrum and Conventional Quantum Characteristics. The results from generators 24A and 24B can then be combined as discussed above.

Figure 7:
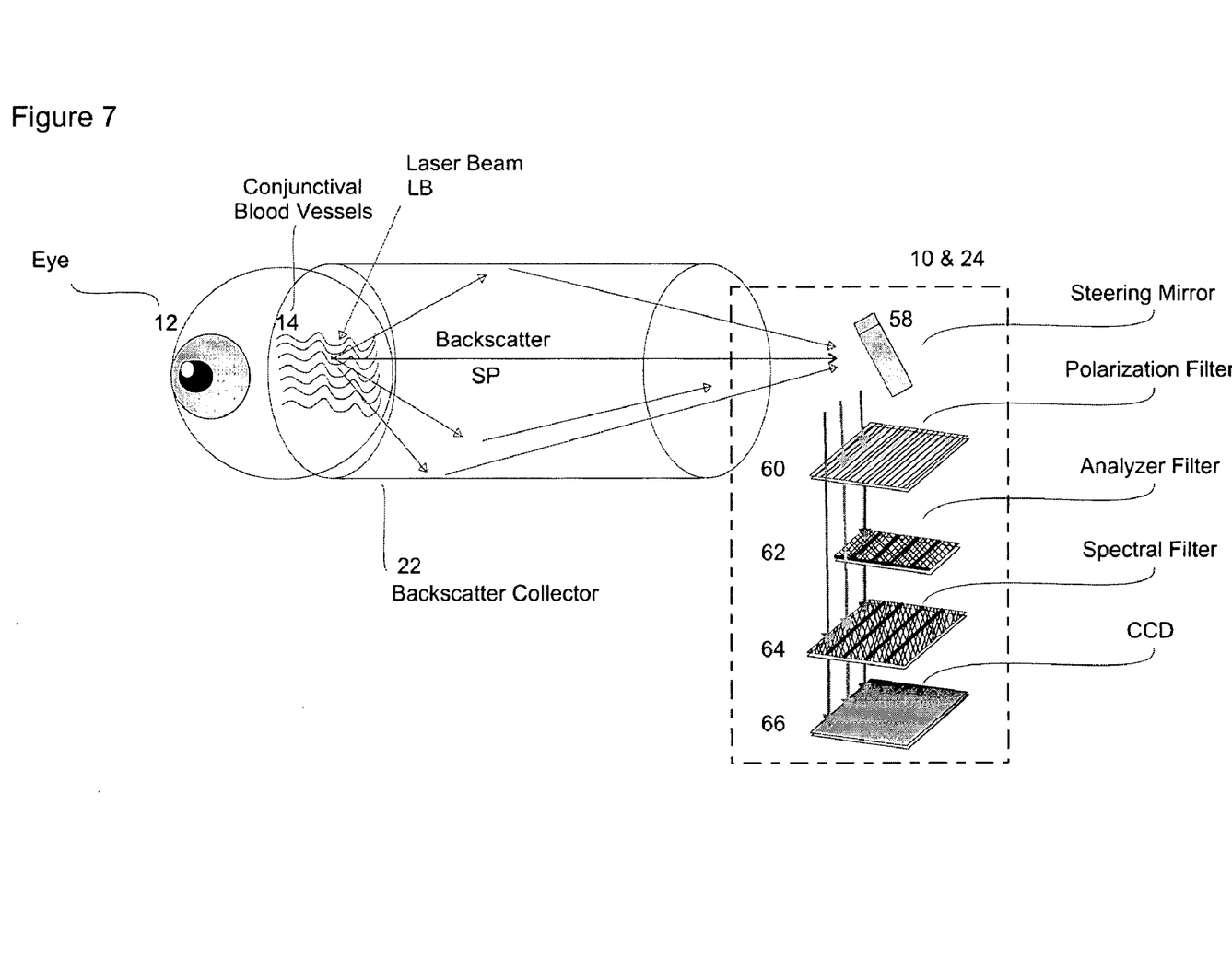
FIG. 7 shows details of the Raman spectrum generator of the apparatus of FIGS. 1, 4 or 6.

FIG. 7 shows details of a Raman spectrum generator and Entangled Quantum Characteristic Generator 24 receiving the beam from the collectors of FIG. 5 and 5. This beam from the collector 22 is transmitted to spectrum analyzer 24 that consists of a steering mirror 58 and several superimposed layers that may have a square, rectangular, oval or other geometric shape. These superimposed layers are set up to allow the beam to be swept along their length so as to pass through different combinations of layers. The steering mirror 58 directs the beam first towards a spectral filter such as a holographic notch filter 64 and through to a photon detector (CCD) 66. This yields Raman shift peaks. The beam is then swept further along so that it passes through a polarization filter 60 and on through a holographic notch filter 64 and through to a photon detector (CCD) 66. This yields information of only portions of the beam that are polarized in a direction A. Next, the beam is then swept further along the so it passes through again a polarization filter 60 and on through to a secondary polarization filter, the analyzer filter 62, a holographic notch filter 64 and through to a photon detector (CCD) 66. The combination of the primary polarization filter 60 and the Polarization analyzer filter 62 yields the sample depolarization ratio. This can be converted to analyte concentration. If the orientations of the polarization filters are changed with respect to the probe beam polarization specific vibrational modes of an analyte can be determined. This will further help delineate analytes from confounding signals.

The spectrum analyzer can be either a high or a low-resolution analyzer. Deciding which spectrometer is appropriate will depend on the specific application.

High-resolution spectrometers could be easily applied to this invention, because they are exquisite at single spectrum analysis. This platform would be wonderfully adept at screening for the presence of multiple biological and chemical analytes. This would nicely apply to a hospital setting where new patients are being screened for unknown disorders.

In contrast low resolution Raman spectrometers are well suited for repetitive concentration analysis of systems containing of known analytes. Here the application would be better suited to where the same patients may be testing themself repetitively as would a diabetic.

For the sake of (brevity, since a both high and low resolution setups for this invention are similar, an example of a low resolution set is discussed below. Though a high resolution spectrometer could obviously be substituted by any one skilled in the art.

Figure 7A:
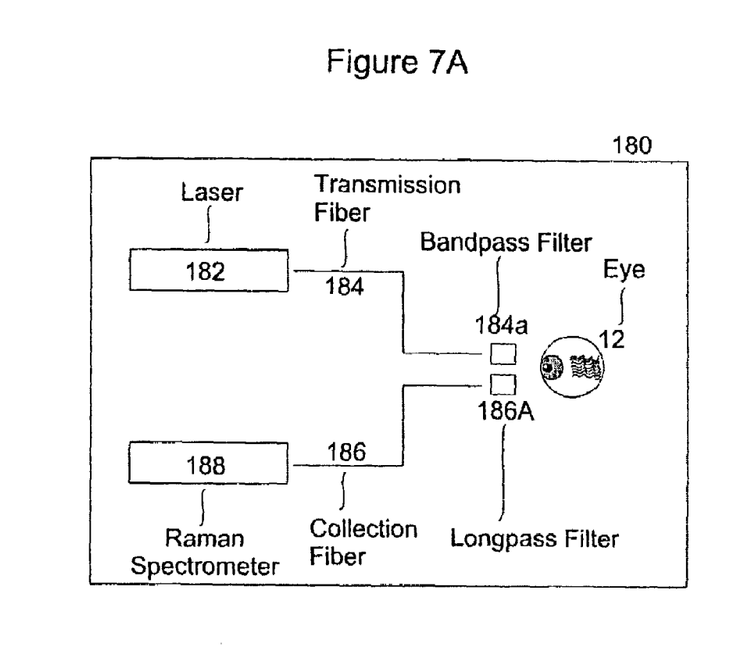
FIG. 7A shows a prior art Raman spectrum generator that can be modified to implement the generator of FIG. 7.

The basic components of a Low Resolution Raman Spectrometer (LRRS) instrument 180 are shown in the schematic illustration of FIG. 7A. The instrument includes a multimode laser diode 182 and a bifurcate fiber optic bundle consisting of a delivery arm in the form of a transmission fiber 184 and a collecting arm or collection fiber 186. The output of the laser 182 is injected into the transmission fiber 184 which then delivers the laser beam to the sample. The tip of the transmission fiber 184 is provided with a bandpass filter 184A that removes silica-Raman frequencies and fiber fluorescence from the excitation beam. The collection fiber 186 is tipped with a long-pass filter 186A for Rayleigh and anti-Stokes Raman scattered light rejection. This type of LRRS instrument is available as the Raman Systems R-2001 manufactured by Boston Advanced Technologies (Marlboro, Mass., USA) and Ocean Optics (Dunedin, Fla., USA). It uses a 785 nm multimode solid-state diode laser provided by Power Technologies. (Little Rock, Ark., USA), adjusted to deliver 400 mW to the sample, and an Ocean Optics S-2000 miniature spectrometer as the Raman spectrometer 188. The diode laser 182 provides a 2 nm wide excitation line. In the present invention, this laser is replaced with one that will produce in the UV wavelength which is then downconverted to the near-infrared range. The S-2000 uses an uncooled 2048-element linear silicon CCD array to measure spectra from 0 to 2700 $cm^{-1}$. The estimated sensitivity of the array elements is 86 photons per count and their well depth at 600 nm is 350 000 photons. The S-2000 uses a single dispersion grating with a line density of 1200 lines/mm. With the 50 micrometer slit selected, the S-2000 has a spectral resolution of approximately 20/cm. The resulting overall resolution of the R-2000 is approximately 30 cm.

The LRRS instrument is modified in the present invention in that it uses a different sample illumination system. While the above LRRS uses conventional laser light to cause Raman back scattering, the invention use the laser source generating monochromatic, coherent, polarized, quantum polarization and or frequency state entangled, exclusively or nearly exclusive co-incident photon pairs as described above. This allows for dramatically attenuating the probe beam while still achieving a strong spectral signal at or below the MPE for ocular tissue. Of course, the other modification is that the ends of the fiber bundles are directed by the tracking mechanism to scan the eye of a patient as discussed above.

Figure 8:
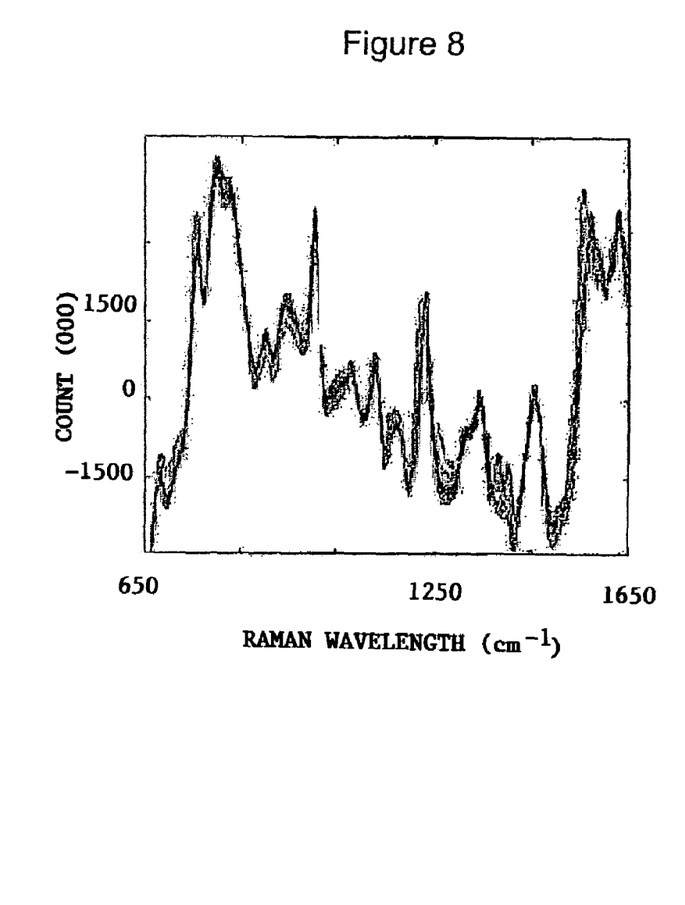
FIG. 8 shows a typical Raman spectrum for glucose.

A typical Raman spectrum characteristic of the glucose content of the blood is shown in FIG. 8. The amplitude of the signal is indicative of the glucose concentration. Alternatively, the concentration is obtained from the depolarization ratio, available from the Quantum state analyzer which in this case is a polarization anlayzer.

The apparatus for making blood analysis may be structured and arranged to perform in several modes of operation. For example, the whole apparatus can be set up in a doctor's office, a hospital, or a private lab, and the blood analysis results can be made available as soon as the computations are completed. Alternatively, the apparatus without the analyzer 26 may be placed in a doctor's office or even a patient's home. The analyzer 26 may be placed in a remote, central location. The raw data collected, is sent to this remote location and then analyzed. The results are then sent back to the physician or the patient electronically, by voice, and/or in the form of a hard copy.

Figure 9:
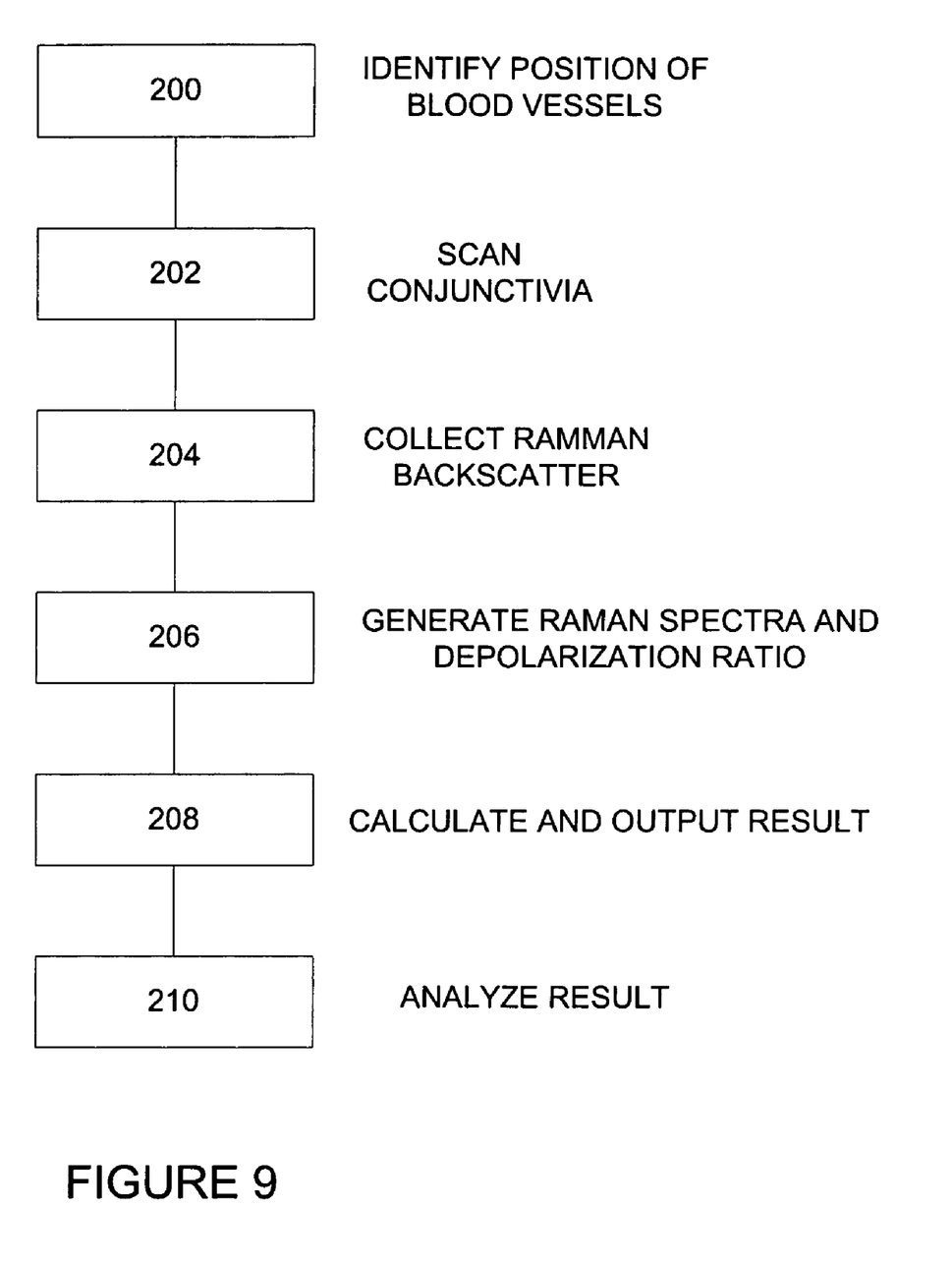
FIG. 9 shows a flow chart describing the operation of the apparatus of FIG. 1.

In FIG. 9 shows a block diagram of the process used by the apparatus of FIG. 1. In step 200 the positions of the blood vessel are identified. In step 202 the conjunctive is scanned with the laser beam from generator 18. For the embodiment of FIG. 1, the laser beam is directed at the blood vessels whose positions have been determined in step 200. Alternatively, the eye is scanned randomly or in a predetermined pattern and photons are directed at various blood vessels distributed on the surface of the eye. The tracking mechanism insures that during this process photons are not directed into the eye through the pupil.

In step 204 the Raman scatter resultant from the photons is collected.

In step 206 the Raman scatter is provided to the Raman spectrum generator 24. In step 208 the desired Raman spectrum including frequency, amplitude, depolarization ratio or other similar parameters are obtained by the Raman spectrum generator 24.

In step 210 these parameters of the Raman spectrum are analyzed by the analyzer and then the results are presented in any desired form.

The embodiments of FIGS. 4 and 6 are operated in the same manner.

The apparatus described above can be used to apply Raman back scatter to directly or indirectly detect various blood parameters and components such as:

Acidity, Alcohol, Ammonia, Amylase, Ascorbic Acid, Bicarbonate, Bilirubin, Blood Volume, Calcium, Carbon Dioxide Pressure, Carbon Monoxide, CD4 Cell Count, Ceruloplasmin, Chloride, CBC, Copper, Creatine Kinase (CK or CPK), Creatine Kinase Isoenzymes, Creatinine, Electrolytes, Glucose, Hematocrit, Hemoglobin, Iron ,Iron-Binding Capacity, Lactate, Lactic Dehydrogenase, Lead, Lipase, Zinc,Cholesterol Triglycerides, Liver Function Tests, Magnesium, Mean Corpuscular Hemoglobin, Mean Corpuscular Hemoglobin Volume, Osmolality, Oxygen Pressure, Oxygen Saturation, Phosphatase Prostatic, Phosphatase, Phosphorous, Platelet Count, Potassium, Prostate Specific Antigen, Protein Total, Protein Albumin, Protein Globulin, Prothrombin, Pyruvic Acid, Red Blood Cell Count, Sodium, Thyroid, Stimulating Hormone, Alanine, Aspartate, Urea Nitrogen, Bun/Creatinine Ratio, Uric Acid, Vitamin A, White Blood Cell Count, etc. The Raman spectrum, polarization and other characteristics for each of these composite materials are obtained either from the literature or by testing a sample of each material in vitro and storing the respective characteristics in a library.

Numerous other modifications may be made to the invention without departing from its scope as defined in the appended claims.

I claim:

1. An apparatus for performing in-vivo blood analysis comprising:
    a laser beam source generating a laser beam with photons arranged in entangled pairs;
    a laser deflection system adapted to direct said laser beam at the blood vessels of the eye of a patient;
    a collector receiving a portion of said laser beam scattered by said blood vessels; and
    an analyzer receiving said portion and generating an output indicative of the composition of the blood in said blood vessels.

2. The apparatus of claim 1 wherein said collector collects Raman back scatter.

3. The apparatus of claim 1 wherein said laser source generates two coincident laser beams.

4. The apparatus of claim 1 wherein said laser source splits the laser beam into first and second beams, said first and second beams consisting of the respective photons of entangled pairs, with the first beam being adapted to be directed toward the patient's eye and the second beam is analyzed to determine characteristics of said first beam after the first beam is scattered.

5. The apparatus of claim 1 wherein said laser source generates said laser beam near an infrared region.

6. An apparatus for performing in-vivo blood analysis comprising:
    a laser beam source generating a first laser beam and a second laser beam, said laser beams consisting of respective first and second photons, each first photon being entangled to a respective second photon;
    a laser deflection system adapted to direct said first laser beam at the blood vessels of the eye of a patient; and
    an analyzer receiving said second laser beam and generating an output indicative of the composition of the blood in said blood vessels.

7. The apparatus of claim 6 wherein said analyzer does not receive said first beam.

8. The apparatus of claim 6 wherein said analyzer includes a first analyzer portion receiving a portion of said first laser beam and a second analyzer portion receiving at least a portion of said laser beam, said analyzer portions analyzing said laser beams to generate a spectrum associated with the patient's blood.

9. The apparatus of claim 8 wherein said analyzer portions generate Raman spectrums.

10. The apparatus of claim 6 wherein said analyzer also receives photons scattered from said first beam and generates a result dependent on said first and second beams.

11. A method of analyzing the blood of a patient comprising:
    generating a stream of photons arranged in entangled pairs;
    directing said stream of photons at the blood vessels of an eye of the patient;
    collecting photons scattered from said blood vessels;
    generating a signal from said scattered photons indicative of said composition; and
    outputting said signal to indicate said composition.

12. The method of claim 11 wherein said scattered photons are indicative of Raman back scatter.

13. The method of claim 12 wherein said step of generating includes generating a plurality of coincident photon beams.

14. The method of claim 13 wherein said coincident photon beams are generated using spontaneous parametric down conversion.

15. The method of claim 11 wherein the laser beam has a wavelength near infrared.

16. The method of claim 11 directing said beam at said eye in a predetermined pattern.

* * * * *